United States Patent [19]

Siegle et al.

[11] 4,006,244
[45] Feb. 1, 1977

[54] BENZO-1,3-DIOXOLAN-4-YL N-METHYL-N-PHENYLMERCAPTO-CARBAMATES

[75] Inventors: Peter Siegle, Cologne; Engelbert Kühle, Bergisch-Gladbach; Gerhard Zümach; Ingeborg Hammann, both of Cologne; Bernhard Homeyer, Opladen, all of Germany

[73] Assignee: Bayer Aktiengesellschaft, Leverkusen, Germany

[22] Filed: May 23, 1975

[21] Appl. No.: 580,380

[30] Foreign Application Priority Data

June 15, 1974 Germany .......................... 2428924

[52] U.S. Cl. .............................. 424/282; 260/340.5; 260/340.9
[51] Int. Cl.² .......................................... A61K 31/34
[58] Field of Search ................. 260/340.5; 424/282

[56] References Cited

UNITED STATES PATENTS

| 3,509,200 | 4/1970 | Elpern et al. | 260/340.5 X |
| 3,663,594 | 5/1972 | Brown et al. | 71/98 X |

Primary Examiner—Ethel G. Love
Attorney, Agent, or Firm—Burgess, Dinklage & Sprung

[57] ABSTRACT

Benzo-1,3-dioxolan-4-yl N-methyl-N-phenylmercaptocarbamates of the formula

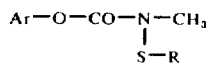

in which
Ar is benzo-1,3-dioxolan-4-yl and
R is phenyl or phenyl substituted by at least one of halogen, nitro, alkyl and trifluoromethyl, which possess insecticidal, fungicidal and bactericidal properties.

8 Claims, No Drawings

BENZO-1,3-DIOXOLAN-4-YL N-METHYL-N-PHENYLMERCAPTO-CARBAMATES

The present invention relates to and has for its objects the provision of particular new benzo-1,3-dioxalan-4-yl or 1,3-dioxolan-2-yl-phenyl-(2) N-methyl-N-phenylmercapto-carbamates which possess insecticidal, fungicidal and bactericidal properties, active compositions in the form of mixtures of such compounds with solid and liquid dispersible carrier vehicles, and methods for producing such compounds and for using such compounds in a new way especially for combating pests, e.g., insects, fungi and bacteria, with other and further objects becoming apparent from a study of the within specification and accompanying examples.

It has been disclosed in published Netherlands Patent Application 68 02492 and 65 13024 that N-methylcarbamates of benzo-1,3-dioxolan-4-ol and 2-(1,3-dioxolan-2-yl)-phenol exhibit an insecticidal action.

However, a disadvantage of these compounds is their high toxicity to warm-blooded animals and the fact that their insecticidal action is not always satisfactory, especially if low concentrations are used.

The present invention provides N-sulfenylated arylcarbamates of the general formula $$Ar-O-CO-N-CH_3 \atop | \atop S-R \qquad (I)$$

in which
Ar is benzo-1,3-dioxolan-4-yl and
R is phenyl or phenyl substituted by at least one of halogen, nitro, alkyl and trifluoromethyl, or
Ar is 1,3-dioxolan-2-yl-phenyl-(2) and
R is phenyl or phenyl substituted by at least one of halogen, nitro, alkyl, 2-trifluoromethyl and 4-trifluoromethyl.

The preferred compounds are those of formula (I) which are sulfenylated arylcarbamates in which Ar is benzo-1,3-dioxolan-4-yl and R is tolyl, ethylphenyl, fluorophenyl, bromophenyl, nitrophenyl or especially trifluoromethylphenyl, chlorophenyl or phenyl, or arylcarbamates in which Ar is 1,3-dioxolan-2-yl-phenyl-(2) and R is phenyl, chlorophenyl, 2-trifluoromethylphenyl, 4-trifluoromethylphenyl, 2-trifluoromethyl-3-chlorophenyl, 2-trifluoromethylphenyl-4-chlorophenyl, 4-trifluoromethyl-2-chlorophenyl, 4-trifluoromethyl-3-chlorophenyl, tolyl, ethylphenyl, fluorophenyl, bromophenyl or nitrophenyl.

Surprisingly, the N-sulfenylated arylcarbamates according to the invention exhibit a substantially better insecticidal, and above all soil-insecticidal, action than the known benzo-1,3-dioxolan-4-yl N-methylcarbamate. Further, the N-sulfenylated arylcarbamates according to the invention are substantially less toxic to warm-blooded aminals than the corresponding nonsulfenylated carbamates. The compounds according to the invention thus represent a genuine enrichment of the art.

The invention also provides a process for the preparation of an N-sulfenylated arylcarbamate of the formula (I) in which a. an N-sulfenylated arylcarbamic acid halide of the general formula $$CH_3-N-CO\ X \atop | \atop S-R \qquad (II)$$

in which
R has the abovementioned meaning and
X is fluorine or chlorine is reacted with a compound of the general formula $$Ar-OH \qquad (III)$$

in which
Ar has the abovementioned meaning optionally in the presence of a diluent and of an acid-binding agent,
or
b. a sulfenyl chloride of the general formula $$R-S-Cl \qquad (IV)$$

in which
R has the abovementioned meaning is reacted with a carbamate of the general formula $$Ar-O-CO-NH-CH_3 \qquad (V)$$

in which
Ar has the abovementioned meaning, optionally in the presence of a diluent and of an acid-binding agent.

If benzo-1,3-dioxolan-4-ol and N-methyl-N-phenyl-mercaptocarbamic acid fluoride are used, the course of the reaction can be represented by the following equation:

If benzo-1,3-dioxolan-4-ol N-methylcarbamate and phenylsulfenyl chloride are used, the course of the reaction can be represented by the following equation:

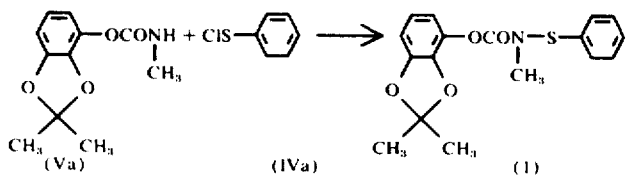

The arylcarbamic acid halides of the general formula (II) used as starting materials are known (German Published Specification DAS No. 1,297,095). The phenols of the formula (III) and the carbamates of the formula (V) may be prepared in accordance with processes described in published Netherlands Patent Applications 65 13024 and 68 02492.

Diluents which can be used in the reaction according to the invention are all inert organic solvents. These include ethers such as diethyl ether, dioxane and tetrahydrofuran, hydrocarbons such as benzene and toluene, and chlorinated hydrocarbons such as chloroform and chlorobenzene.

To bind hydrogen halide liberated in the reaction, an acid-binding agent, preferably a tertiary organic base such as triethylamine, is preferably added to the reaction mixture.

If desired, the compounds of the formula (III) may be used in the form of alkali metal salts.

The reaction temperatures can be varied within a substantial range; in general, the reaction is carried out at 0° to 100° C, preferably at 20° to 40° C.

As already mentioned, the new N-substituted carbamates are distinguished by an excellent insecticidal, above all soil-insecticidal, action. Furthermore, the compounds according to the invention are distinguished by their low toxicity to warm-blooded animals, compared with the unsubstituted carbamates on which they are based.

The compounds can therefore be employed particularly advantageously for combating sucking and biting insects, including hygiene pests and pests of stored products, as well as soil insects. They furthermore possess a soil-fungicidal and bacteriostatic action.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

When applied against hygiene pests and pests of stored products, particularly flies and mosquitoes, the novel products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, fungicides and bactericides, or acaricides, nematocides, herbicides, fertilizers, growth-regulating agents, etc., if desired, or in the form of particular dosage preparations for specific applications made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g., insects, fungi and bacteria, and more particularly methods of combating insects, which comprises applying to at least one of correspondingly (a) such insects, (b) such fungi, (c) such bacteria, and (d) the corresponding habitat thereof, i.e., the locus to be protected, e.g., to a growing crop, to an area where a crop is to be grown or to a domestic animal, a correspondingly combative or toxic amount, i.e., an insecticidally, fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 1.

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance; only the amount by weight of active compound per unit volume of soil, which is given in ppm (= mg/l), was decisive. The soil was filled into pots and the pots were left to stand at room temperature.

After 24 hours, the test insects were introduced into

Table 1

| (Insects which damage plants) | | |
|---|---|---|
| Active compounds | Active compound concentration in % by weight | Degree of destruction in % after 3 days |
| [structure, known] | 0.01<br>0.001 | 100<br>0 |
| [structure (1)] | 0.01<br>0.001 | 100<br>100 |
| [structure (2)] | 0.01<br>0.001 | 100<br>75 |
| [structure (3)] | 0.01<br>0.001 | 100<br>85 |

EXAMPLE 2

Critical concentration test/soil insects

Test insect: *Phorbia antiqua* - grubs
Solvent: 3 parts by weight of acetone
Emulsifier: 1 part by weight of alkylaryl polyglycol ether the treated soil and after a further 2 to 7 days the degree of effectiveness of the active compound was determined in % by counting the dead and live test insects. The degree of destruction is 100% if all test insects had been killed and is 0% if just as many test insects were still alive as in the case of control.

The active compounds, the amounts used and the results can be seen from Table 2 which follows:

Table 2

| Soil Insecticides | | |
|---|---|---|
| *Phorbia antiqua* grubs in the soil | | |
| Active compound | Active compound concentration in ppm | Degree of destruction in % |
| [structure, known] | 10 | 0 |

Table 2-continued

Soil Insecticides
Phorbia antiqua grubs in the soil

| Active compound | Active compound concentration in ppm | Degree of destruction in % |
|---|---|---|
| (2) structure with CF₃ | 10 | 100 |
| (1) structure | 10 | 100 |
| (3) structure with Cl | 10 | 100 |

EXAMPLE 3

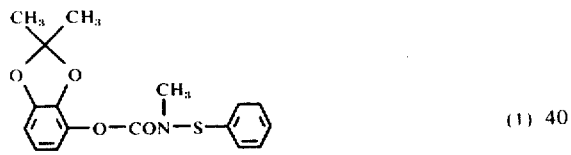 (1)

16.6 g (0.1 mole) of benzo-1,3-dioxolan-4-ol and 18.6 g (0.1 mole) of N-methyl-N-phenylmercaptocarbamic acid fluoride were dissolved in 250 ml of absolute toluene at room temperature and 11 g (0.11 mole) of triethylamine were added. In the course thereof, the temperature did not rise above 40° C. After stirring for a further two hours, water was added to the cold mixture and the organic phase was separated off, washed with water and dried. After evaporating off the solvent, an oil of refractive index $n_D^{25} = 1.5626$ remained.

Yield 28 g.

The following were prepared analogously:

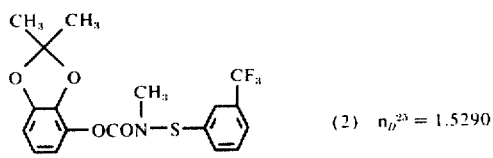 (2) $n_D^{25} = 1.5290$

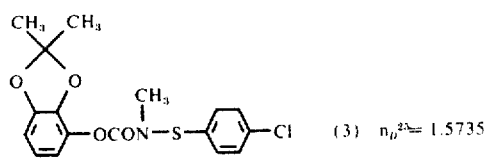 (3) $n_D^{25} = 1.5735$

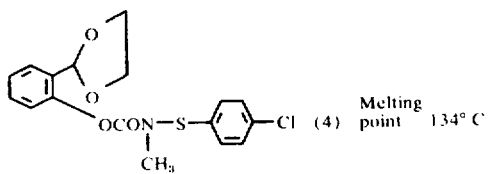 (4) Melting point 134° C

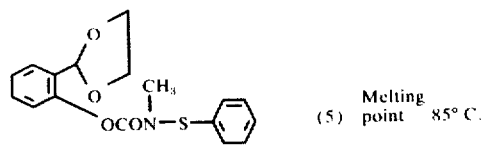 (5) Melting point 85° C.

Other compounds which can be similarly prepared include:

2,2-dimethyl-benzo-1,3-dioxolan-4-yl N-methyl-N-p-tolylmercapto-carbamate,
2,2-dimethyl-benzo-1,3-dioxolan-4-yl N-methyl-N-m-ethylphenylmercapto-carbamate,
2,2-dimethyl-benzo-1,3-dioxolan-4-yl N-methyl-N-p-fluorophenylmercapto-carbamate,
2,2-dimethyl-benzo-1,3-dioxolan-4-yl N-methyl-N-p-bromophenylmercapto-carbamate,
2,2-dimethyl-benzo-1,3-dioxolan-4-yl N-methyl-N-o-nitrophenylmercapto-carbamate,
1,3-dioxolan-2-yl-phenyl-(2) N-methyl-N-3'-trifluoromethylphenylmercapto-carbamate,
1,3-dioxolan-2-yl-phenyl-(2) N-methyl-N-4'-trifluoromethylphenylmercapto-carbamate,
1,3-dioxolan-2-yl-phenyl-(2) N-methyl-N-(3'-chlorophenylmercapto)-carbamate,
1,3-dioxolan-2-yl-phenyl-(2) N-methyl-N-(3'-trifluoromethyl-4'-chlorophenylmercapto)-carbamate,
1-3-dioxolan-2-yl-phenyl-(2) N-methyl-N-4'-trifluoromethyl-2'-chlorophenylmercapto)-carbamate,
1-3-dioxolan-2-yl-phenyl-(2) N-methyl-N-4'-trifluoromethyl-3'-chlorophenylmercapto)-carbamate,
1,3-dioxolan-2-yl-phenyl-(2) N-methyl-N-p-tolylmercapto-carbamate, 1,3-dioxolan-2-yl-phenyl-(2) N-m-ethylphenylmercapto-carbamate, 1,3-dioxolan-2-yl-phenyl(2) N-p-fluorophenylmercapto-carbamate, 1,3-dioxolan-2-yl-phenyl(2) N-p-bromophenylmercapto-carbamate, 1,3-dioxolan-2-yl-phenyl(2) N-o-nitrophenylmercapto-carbamate, and the like.

It will be appreciated that the instant specification and examples are set forth by way of illustration and not limitation, and that various modifications and changes may be made without departing from the spirit and scope of the present invention.

What is claimed is:

1. A benzo-1,3-dioxolan-4-yl N-methyl-N-phenylmercapto-carbamate of the formula

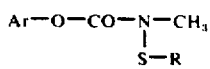

in which

Ar is benzo-1,3-dioxolan-4-yl and

R is phenyl or phenyl substituted by at least one of halogen, nitro, alkyl and trifluoromethyl.

2. A compound according to claim 1 in which Ar is benzo-1,3-dioxolan-4-yl and R is phenyl, tolyl, ethylphenyl, fluorophenyl, chlorophenyl, bromophenyl, nitrophenyl or trifluoromethylphenyl.

3. The compound according to claim 1 wherein such compound is 2,2-dimethyl-benzo-1,3-dioxolan-4-yl N-methyl-N-phenylmercapto-carbamate of the formula

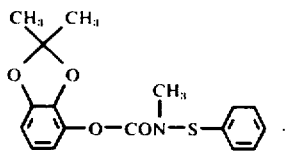

4. The compound according to claim 1 wherein such compound is 2,2-dimethyl-benzo-1,3-dioxolan-4-yl N-methyl-N-3'-trifluoromethylphenylmercapto-carbamate of the formula

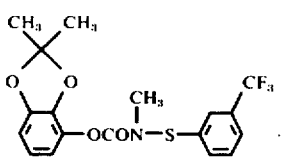

5. The compound according to claim 1 wherein such compound is 2,2-dimethyl-benzo-1,3-dioxolan-4-yl N-methyl-N-p-chlorophenylmercapto-carbamate of the formula

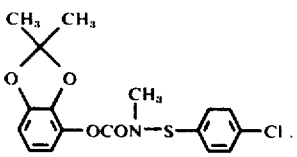

6. An insecticidal composition containing as active ingredient an insecticidally effective amount of a compound according to claim 1 in admixture with a diluent.

7. A method of combating insect pests which comprises applying to the pests or a habitat thereof an insecticidally effective amount of a compound according to claim 1.

8. The method according to claim 7 in which said compound is 2,2-dimethyl-benzo-1,3-dioxolan-4-yl N-methyl-N-phenylmercapto-carbamate, 2,2-dimethyl-benzo-1,3-dioxolan-4-yl N-methyl-N-3'-trifluoromethylphenylmercapto-carbamate, or 2,2-dimethyl-benzo-1,3-dioxolan-4-yl N-methyl-N-p-chlorophenylmercapto-carbamate.

* * * * *